United States Patent
Nockemann et al.

(10) Patent No.: US 11,396,684 B2
(45) Date of Patent: Jul. 26, 2022

(54) EXTRACTING RARE EARTH METAL FROM ACIDIC SOLUTION BY CONTACTING WITH IONIC LIQUID COMPOSITION

(71) Applicants: Peter Nockemann, Antrim (GB); Ruhela Ritesh, Antrim (GB)

(72) Inventors: Peter Nockemann, Antrim (GB); Ruhela Ritesh, Antrim (GB)

(73) Assignee: The Queen's University of Belfast, Belfast (GB)

( * ) Notice: Subject to any disclaimer, the term of this patent is extended or adjusted under 35 U.S.C. 154(b) by 206 days.

(21) Appl. No.: 16/469,748

(22) PCT Filed: Dec. 14, 2017

(86) PCT No.: PCT/GB2017/053754
§ 371 (c)(1),
(2) Date: Jun. 14, 2019

(87) PCT Pub. No.: WO2018/109483
PCT Pub. Date: Jun. 21, 2018

(65) Prior Publication Data
US 2020/0080169 A1     Mar. 12, 2020

(30) Foreign Application Priority Data
Dec. 16, 2016  (GB) ..................................... 1621523

(51) Int. Cl.
| C22B 3/00 | (2006.01) |
| C22B 3/36 | (2006.01) |
| C22B 59/00 | (2006.01) |
| C22B 3/28 | (2006.01) |

(52) U.S. Cl.
CPC .............. *C22B 3/362* (2021.05); *C22B 3/288* (2021.05); *C22B 59/00* (2013.01)

(58) Field of Classification Search
CPC ......... C22B 59/00; C22B 3/288; C22B 3/362; C07C 211/63; C07D 233/61
See application file for complete search history.

(56) References Cited

U.S. PATENT DOCUMENTS 4,016,237 A     4/1977   Mason et al.

FOREIGN PATENT DOCUMENTS

| CN | 103451427 A | 12/2013 |
| CN | 103961978 A | 8/2014 |
| CN | 106498184 A | 3/2017 |
| JP | 2010518019 A | 5/2010 |
| JP | 5279938 B1 | 9/2013 |
| JP | 5889455 B1 | 3/2016 |
| WO | 2007071028 A1 | 6/2007 |
| WO | 2010116167 A1 | 10/2010 |
| WO | 2013128536 A1 | 9/2013 |
| WO | 2015106324 A1 | 7/2015 |

OTHER PUBLICATIONS

Shkrob et al, "Ionic liquid based separations of trivalent lanthanide and actinide ions" I&EC Research, 53(9), pp. 3641-3653. (Year: 2014).*
United Kingdom Search Report dated Aug. 1, 2017, App. No. GB1621523.8.
International Search Report dated Feb. 20, 2018; PCT/GB2017/053754.
Yinghui Liu; Ji Chen and Deqian Li; "Application and Perspective of Ionic Liquids on Rare Earths Green Separation"; Separation Science and Technology; vol. 47, pp. 223-232, 2012.

* cited by examiner

*Primary Examiner* — Steven J Bos
(74) *Attorney, Agent, or Firm* — Ryan T. Grace; Advent, LLP (57) ABSTRACT

A method for extracting a rare earth metal from a mixture of one or more rare earth metals, said method comprising contacting an acidic solution of the rare earth metal with a composition which comprises an ionic liquid to form an aqueous phase and a non-aqueous phase into which the rare earth metal has been selectively extracted.

23 Claims, 2 Drawing Sheets

EXTRACTING RARE EARTH METAL FROM ACIDIC SOLUTION BY CONTACTING WITH IONIC LIQUID COMPOSITION

The present invention relates to the extraction and separation of rare earth metals. In particular, the present invention relates to the extraction and separation of rare earth metals using specifically designed ionic liquids.

BACKGROUND

Rare earth Metals, which include the lanthanides (La to Lu), Y, and Sc, have unique physicochemical properties which make them crucial components of numerous high-tech products and environmental technologies such as wind mills, LCD/LED displays, phosphors, magnet drives (hard disk), and others. These applications demand a continuous supply of high purity rare earth metals to the industries, which is currently met by mining and processing the natural ores of these metals. However, there are concerns that the exponentially increasing demand of these metals will surpass the supply in coming years and therefore, it has become attractive to explore other secondary sources of these valuable metals. One such source is the recovery of rare earth metals from end-of-life and manufacturing wastes materials (often referred to as "urban mining"), which, though quite challenging, can potentially provide a continuous supply of the rare earth metals. One of most important requirements of urban mining is the development of cost effective and robust separation processes/technologies which allow selective and efficient separation of rare earth metals from each other (intra-group separation) to provide high purity rare earth metals.

During the last five decades various processes such as liquid-liquid extraction (e.g. Rhône-Poulenc process), ion exchange, and precipitation have been developed. Among the various available technologies, liquid-liquid extraction has been found to be the most suitable commercial process owing to its scalability, adaptability, and recyclability. Additionally, the liquid-liquid extraction processes used to date employ commercial organophosphorus extractants which do not possess specific selectivity for individual rare earth metals, thereby leading to a number of stages to separate rare earth metals from each other (see Table 1). Furthermore, additional processing steps are generally required to recover the rare earth metal in high purity. These factors lead to manifold increase in processing costs thereby putting strain on overall costing of consumer products. Also, most employed methods for the separation of rare earth metals necessitate the use of organic solvents, which due to their toxicity, volatility and flammability are not considered environmentally friendly.

Some of the currently used industrial liquid-liquid extraction processes available for intra-group separation of rare earth metals (e.g. separation of dysprosium from neodymium) are compared in Table 1.

The separation factor for an individual rare earth metal pair is expressed as the ratio of the distribution ratios ($D_M$) of the rare earth metals, where the distribution ratio of an individual rare earth metal is determined as the ratio of its concentration in the non-aqueous phase to that in the aqueous phase i.e. $D_M=[M]_{N-Aq}/[M]_{Aq}$. For example, the separation factor of Dysprosium with respect to Neodymium=$D_{Dy}/D_{Nd}$.

TABLE 1

Comparison of the separation factors of commonly used REM extractants.

| Liquid-liquid extraction | Major component | Separation factor | Reference |
|---|---|---|---|
| HDEHP process | Bis-(2-ethylhexyl)-phosphoric acid | 41.5 (Dy/Nd) | C. K. Gupta, N. Krishnamurthy, Extractive Metallurgy of Rare Earths, CRC, New York, 2005, pp. 1-484. |
| Cyanex 272 process | Bis-(2,4,4-trimethylpentyl)phosphinic acid | 1.36 (Dy/Nd) | B. Swain, E. O. Otu, Separation and Purification Technology, 83, (2011), 82-90 |
| Cyanex 302 process | Bis-(2,4,4-trimethylpentyl)-monothiophosphinic acid | 239.3 (Dy/Nd) | M. Yuan, A. Luo, D. Li, Acta Metall. Sin. 1995, 8, 10-14. |
| Synergist process | 2-ethylhexylphosphonic acid mono-(2-ethylhexyl)ester; sec-nonylphenoxy acetic acid | 1.17 (Dy/Nd) | N. Song, S. Tong, W. Liu, Q. Jia, W. Zhoua and W. Liaob, J. Chem. Technol. Biotechnol., 2009, 84, 1798-1802. |

Another of the most commonly used organophosphorous extractants, P507 (2-ethylhexyl phosphoric acid mono(2-ethylhexyl) ester), also gives low separation factors, with the selectivity for heavy rare earth metals generally being lower than for light rare earth metals (e.g. Tm/Er (3.34), Yb/Tm (3.56), and Lu/Yb (1.78)). Another significant deficiency of many common rare earth metal extractants such as P507 is that it is difficult to strip heavy rare earth metals completely, especially for Tm(III), Yb(III), and Lu(III), even at higher acidity. Low selectivity for rare earth metals results in too many stages required for effective separation, the low extractability of rare earth metals demanding the use of higher concentrations of the extractant. The production of organophosphorous extractants also requires complicated synthetic procedures starting from hazardous starting materials and the stability and recyclability of these extractants is limited. Emulsification and leaching of extractants has been identified as another common problem.

A chelating diamide extractant attached to a silica support was reported by Fryxell et al. for the separation of lanthanides (*Inorganic Chemistry Communications*, 2011, 14, 971-

974). However, this system was unable to extract rare earth metals under acidic conditions (pH<5) and crucially showed very low uptake and separation factors between rare earth metals.

Ionic liquids have also been used as potential extractants for rare earth metals. Binnemans et al. reported the extraction of Nd and Dy or Y and Eu from mixtures of transition metal compounds with a betainium bis(trifluoromethylsulfonyl)imide ionic liquid (*Green Chemistry*, 2015, 17, 2150-2163; *Green Chemistry*, 2015, 17, 856-868). However, this system was unable to selectively perform intra-group separation between rare earth metals.

Chai et al. reported the use of an ionic liquid based on 2-ethylhexyl phosphonic acid mono(2-ethylhexyl) ester (P507) with a trioctylmethylammonium cation for separation of rare earth metals (*Hydrometallurgy*, 2015, 157(C), 256-260). In this case only low distribution factors and separation factors were observed, indicating a lack of extractability and selectivity. In addition, during recovery of the rare earth metal from the ionic liquid, the acid added will decompose the acid-base pair ionic liquid, which must then be regenerated by metathesis.

Separation of Nd and Dy was reported by Schelter et al., whereby separation was achieved by precipitation using a tripodal nitroxide ligand to form Nd and Dy complexes with differing solubilities in benzene. However, precipitation is not considered to be a commercially viable process and, in addition, the process requires the use of specific rare earth metal precursors and an inert, moisture-free environment, which is highly impractical for commercial scale up. This method also relies on the use of benzene to achieve high separation, which is a very toxic solvent.

Therefore, there is a need for the development of effective processes that enhance separation selectivity and extractability, whilst minimizing environmental pollution.

By using an ionic liquid having a cation comprising particular features, it has been found that rare earth metals may be extracted and separated from each other with increased selectivity and extractability in comparison to known methods using different extractants. As the method uses an ionic liquid, the extractant can also provide decreased volatility and flammability, potentially leading to safer and more environmentally friendly rare earth metal extraction.

Thus, in a first aspect, the present invention provides a method for extracting a rare earth metal from a mixture of one or more rare earth metals, said method comprising contacting an acidic solution of the rare earth metal with a composition which comprises an ionic liquid to form an aqueous phase and a non-aqueous phase into which the rare earth metal has been selectively extracted, wherein the ionic liquid has the formula:

[Cat⁺][X⁻]

in which:

[Cat⁺] represents a cationic species having the structure:

where: [Y⁺] comprises a group selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups;

each EDG represents an electron donating group; and $L_1$ represents a linking group selected from $C_{1-10}$ alkanediyl, $C_{2-10}$ alkenediyl, $C_{1-10}$ dialkanylether and $C_{1-10}$ dialkanylketone groups;

each $L_2$ represents a linking group independently selected from $C_{1-2}$ alkanediyl, $C_2$ alkenediyl, $C_{1-2}$ dialkanylether and $C_{1-2}$ dialkanylketone groups; and

[X⁻] represents an anionic species.

The term "ionic liquid" as used herein refers to a liquid that is capable of being produced by melting a salt, and when so produced consists solely of ions. An ionic liquid may be formed from a homogeneous substance comprising one species of cation and one species of anion, or it can be composed of more than one species of cation and/or more than one species of anion. Thus, an ionic liquid may be composed of more than one species of cation and one species of anion. An ionic liquid may further be composed of one species of cation, and one or more species of anion. Still further, an ionic liquid may be composed of more than one species of cation and more than one species of anion.

The term "ionic liquid" includes compounds having both high melting points and compounds having low melting points, e.g. at or below room temperature. Thus, many ionic liquids have melting points below 200° C., particularly below 100° C., around room temperature (15 to 30° C.), or even below 0° C. Ionic liquids having melting points below around 30° C. are commonly referred to as "room temperature ionic liquids" and are often derived from organic salts having nitrogen-containing heterocyclic cations. In room temperature ionic liquids, the structures of the cation and anion prevent the formation of an ordered crystalline structure and therefore the salt is liquid at room temperature.

Ionic liquids are most widely known as solvents. Many ionic liquids have been shown to have negligible vapour pressure, temperature stability, low flammability and recyclability. Due to the vast number of anion/cation combinations that are available it is possible to fine-tune the physical properties of the ionic liquid (e.g. melting point, density, viscosity, and miscibility with water or organic solvents) to suit the requirements of a particular application.

Typically, when rare earth metals are extracted from sources such as ores or waste materials, the resulting product is a mixture of rare earth metals dissolved in an aqueous acidic solution. In the method according to the present invention, rare earth metals may be selectively extracted directly from an aqueous acidic feed, negating the need to apply significant processing to the feed prior to extraction.

It will be appreciated that in order to form an aqueous phase and a non-aqueous phase when contacted with the acidic solution, the composition comprising an ionic liquid will be sufficiently hydrophobic such that a phase separation will occur between the aqueous solution and the composition.

By the use of the composition comprising an ionic liquid as defined according to the first aspect, it has been surprisingly found that increased selectivity and extractability may be obtained in the extraction of rare earth metals from an acidic solution. The combination of high extractability (indicated by distribution ratio) and selectivity (indicated by separation factors) is key to a commercially effective separation process because the number of separation stages necessary to produce a product may be reduced without sacrificing purity. For example, according to the method of the present invention, mixtures of dysprosium and neodymium may be separated with a selectivity (separation factor) of over 1000:1 in a single contact. This represents a substantial increase over known systems as reported in Table 1.

Without wishing to be bound by any particular theory, it is believed that the presence of the central nitrogen donor atom in the ionic liquid allows for differing binding strengths to different rare earth metals as a result of differing ionic radii due to lanthanide contraction. In this way, some rare earth metals are preferentially bound by the hydrophobic ionic liquid extractant, which results in effective intra-group separation of the rare earth metals. It is believed that the arrangement of this variable nitrogen binding as part of an ionic liquid provides the particularly effective extraction of rare earth metals described herein. Nonetheless, it will be appreciated that the ionic liquid comprising a nitrogen donor, whilst discriminating between different rare earth metals, must have additional electron donating groups appended in order to provide sufficient extractability.

Preferably, the method further comprises recovering the rare earth metal from the non-aqueous phase. This recovery may be performed using any suitable means, however it is preferred that the rare earth metal is recovered from the non-aqueous phase by stripping with an acidic stripping solution.

It will be appreciated that the acidic stripping solution may be any acidic solution which liberates the rare earth metal from the ionic liquid. In most embodiments, the acidic stripping solution will be an aqueous acidic stripping solution and the acid will substantially remain in the aqueous phase on contact with the ionic liquid. Preferably, the acidic stripping solution comprises an aqueous hydrochloric acid or nitric acid solution.

The stripping of the rare earth metal may be conducted in any suitable manner. Preferably, the ionic liquid is contacted with an acidic stripping solution for 2 or more stripping cycles to completely strip the rare earth metal, more preferably 2 or 3 stripping cycles are used. In some embodiments, a single stripping cycle may be used. A "stripping cycle" as referred to herein will typically comprise contacting the acidic stripping solution with the composition, equilibrating for an amount of time, for example 15 to 30 minutes, and separating the aqueous and organic phases. A second cycle may be conducted by contacting the composition with another acidic stripping solution substantially free of rare earth metals.

One advantage of the ionic liquid extractant as described in relation to the first aspect is that the rare earth metal may be stripped from the ionic liquid at a relatively high pH. This saves costs associated with both the amount and the strength of acid needed to strip the rare earth metals from the ionic liquid and the equipment necessary to handle such strong acids. In addition, it is possible to completely strip rare earth metals from the ionic liquid at a relatively high pH, whilst for many known extractants such as P507 it is difficult to completely strip heavy rare earth metals (e.g. Tm(III), Yb(III), Lu(III)) even at low pH.

Thus, the acidic stripping solution preferably has a pH of 0 or higher. In preferred embodiments, the acidic stripping solution has a pH of 1 or lower.

In preferred embodiments, the method comprises extracting a rare earth metal from a mixture of two or more rare earth metals. Preferably, the acidic solution comprises a first and a second rare earth metal, and the method comprises:
(a) preferentially partitioning the first rare earth metal into the non-aqueous phase.

Preferably, the method further comprises, in step (a), separating the non-aqueous phase from the acidic solution; and
(b) contacting the acidic solution depleted of the first rare earth metal with the composition which comprises an ionic liquid, and optionally recovering the second rare earth metal therefrom.

In some preferred embodiments the first rare earth metal is recovered from the non-aqueous phase in step (a), and said non-aqueous phase is recycled and used as the composition in step (b).

It will be appreciated that, because the extractability (distribution factor) for a particular rare earth metal varies with pH, it may be preferred to extract different rare earth metals at different pH levels. For example, the acidic solution may have a lower pH in step (a) in comparison to that in step (b). Preferably, the acidic solution has a pH of less than 3.5 in step (a), and the acidic solution has a pH of greater than 3.5 in step (b). Typically, 2 or 3 extraction cycles will be performed at a particular pH. Although the above embodiment describes extraction in only two different pH values, it will be appreciated that a separation of rare earth metals will usually be conducted across a range of pH values, with a gradual increase in pH and multiple extraction steps. For example, where three or more rare earth metals are separated, several separation steps may be conducted in across a particular pH range, for example from pH 1 to 4.

The acidic solution from which the rare earth metal is extracted may have any suitable pH. Preferably, the rare earth metal is extracted at a pH of more than 1, more preferably at a pH of from 2 to 4.

The pH level of the acidic solution of the rare earth metal may be adjusted in any suitable way, as is well known to those skilled in the art. For example, the pH level of the acidic solution may be altered by the addition of acid scavengers such as mildly alkaline solutions including sodium carbonate, sodium bicarbonate, ammonia, $CO_2$, amines or alcohols.

The above embodiments refer to the separation of a particular rare earth metal from another directly from the acidic solution of the rare earth metal at varying pH levels. However, it will be understood that any suitable extraction sequence may be used to separate rare earth metals. For example, two or more rare earth metals may be extracted from the acidic solution to the non-aqueous phase simultaneously at a higher pH, followed by back-extraction of the non-aqueous phase with acidic solutions having a lower pH to separate individual rare earth metals. Thus, all or only some of the rare earth metals present in the acidic solution may initially be extracted from the acidic solution using the composition comprising the ionic liquid.

It will be appreciated that the separation of certain pairs of rare earth metals are of particular importance due to their simultaneous recovery from valuable waste materials. For example, Nd and Dy are widely used in permanent magnets for numerous applications such as hard disks, MRI scanners, electric motors and generators. La and Eu are also an important pair due to their common use in lamp phosphors, other phosphors include Y and Eu (YOX phosphors); La, Ce and Tb (LAP phosphors); Gd, Ce and Tb (CBT phosphors); and Ce, Tb (CAT phosphors).

Thus, in preferred embodiments, the first rare earth metal is dysprosium, and the second rare earth metal is neodymium. In other preferred embodiments, the first rare earth metal is lanthanum, and the second rare earth metal is europium. In yet other preferred embodiments, the first rare earth metal is terbium, and the second rare earth metal is cerium.

The composition may be contacted with the acidic solution in any suitable manner and in any suitable ratio such that exchange of rare earth metals is achieved between the aqueous and non-aqueous phases.

The composition is preferably added to the acidic solution in a volume ratio of from 0.5:1 to 2:1, preferably 0.7:1 to 1.5:1, more preferably 0.8:1 to 1.2:1, for example 1:1. Nonetheless, it will be appreciated that the volume ratio will vary depending on the manner in which the acidic solution is contacted with the composition comprising the ionic liquid.

Preferably, prior to contacting the composition with the acidic solution of the rare earth metal the composition is equilibrated with an acidic solution having the same pH as the acidic solution of the rare earth metal. In this way, the mixture of the composition and the acidic solution will generally remain at the desired pH level during the extraction.

The composition may be contacted with the acidic solution of the rare earth metal under any conditions suitable for extracting the rare earth metal.

It will be appreciated that the temperature employed during contacting of the acidic solution with the composition comprising the ionic liquid may be any suitable temperature and may vary according to the viscosity of the composition comprising the ionic liquid. For example, where a higher viscosity composition is used, a higher temperature may be necessary in order to obtain optimal results.

Preferably, the acidic solution is contacted with the composition at ambient temperature, i.e. without external heating or cooling. It will nonetheless be appreciated that temperature changes may naturally occur during the extraction as a result of contacting the composition with the acidic solution.

The composition may be contacted with the acidic solution of the rare earth metal for any length of time suitable to facilitate extraction of the rare earth metal into the non-aqueous phase. Preferably, the length of time will be such that an equilibrium is reached and the proportions of rare earth metal in the aqueous and non-aqueous phases are constant. In preferred embodiments, the method comprises contacting the acidic solution of the rare earth metal and the composition for from 10 to 40 minutes, preferably from 15 to 30 minutes.

Preferably, the method comprises contacting and physically mixing the acidic solution of the rare earth metal and the composition. Such mixing will usually speed up extraction of the rare earth metal. Any suitable apparatus may be used to achieve this and mixing apparatus is well known in the art. For example, the mixture may be mixed using an agitator or stirrer. The mixing apparatus may comprise equipment specifically designed for multi-phase mixing such as high shear devices. Alternatively, mixing may comprise shaking the mixture, for example, using a wrist action shaker.

The separation of the aqueous and non-aqueous phases may be performed by any suitable method, for example by use of small scale apparatus such as a separating funnel or Craig apparatus. It will be appreciated that the phases will normally be allowed to settle prior to separation. Settling may be under gravity or preferably accelerated by the use of additional equipment such as centrifuge. Alternatively, aqueous and non-aqueous phases may be separated by the use of equipment which both contacts and separates the phases, for example a centrifugal extractor, a pulsed column, or a combined mixer-settler.

It will be understood that in order to extract or separate some rare earth metals, multiple extractions and separations may be performed. This may involve multiple extractions of the acidic solution of the rare earth metal with the composition or multiple back-extractions of the non-aqueous phase with an aqueous acidic solution. In accordance with the present invention, fewer steps are required to separate rare earth metals due to the ionic liquid extractant giving separation factors and distribution ratios above those typically found in previous systems.

The term electron donating group (EDG) as used herein will be understood to include any group having a pair of electrons available to form a coordinate bond with an acceptor. In particular, it will be appreciated that an electron donating group, as defined herein, refers to groups having an available pair of electrons able to coordinate to a rare earth metal to form a metal-ligand complex. It will also be understood that the EDGs will typically have a single atom from which the electrons are donated to form a bond. However, electrons may alternatively be donated from one or more bonds between atoms, i.e. EDG may represent a ligand with a hapticity of 2 or more.

It will be understood that the arrangement of the EDGs and the linkers $L_2$ will be such that the EDGs and the central nitrogen atom are able to coordinate to a rare earth metal simultaneously.

Preferably, when the nitrogen linking $L_1$ to each $L_2$ and one of the EDG both coordinate to a metal, the ring formed by the nitrogen, $L_2$, the EDG and the metal is a 5 or 6 membered ring, preferably a 5 membered ring.

In preferred embodiments, [$Y^+$] represents an acyclic cation selected from:

wherein: $R^a$, $R^b$ and $R^c$ are each independently selected from optionally substituted $C_{1-30}$ alkyl, $C_{3-8}$ cycloalkyl and $C_{6-10}$ aryl groups.

In other preferred embodiments, [$Y^+$] represents a cyclic cation selected from:

wherein: $R^a$, $R^b$, $R^c$, $R^d$, $R^e$ and $R^f$ are each independently selected from: hydrogen and optionally substituted $C_{1-30}$ alkyl, $C_{3-8}$ cycloalkyl and $C_{6-10}$ aryl groups, or any two of $R^a$, $R^b$, $R^c$, $R^d$ and $R^e$ attached to adjacent carbon atoms form an optionally substituted methylene chain —$(CH_2)_q$— where q is from 3 to 6.

Suitably, in preferred embodiments, at least one of $R^a$, $R^b$, $R^c$, $R^d$, $R^e$ and $R^f$ is a $C_{1-5}$ alkyl group substituted with —$CO_2R^x$, —$OC(O)R^x$, —$CS_2R^x$, —$SC(S)R^x$, —$S(O)OR^x$, —$OS(O)R^x$, —$NR^xC(O)NR^yR^z$, —$NR^xC(O)OR^y$, —$OC(O)NR^yR^z$, —$NR^xC(S)OR^y$, —$OC(S)NR^yR^z$, —$NR^xC(S)SR^y$, —$SC(S)NR^yR^z$, —$NR^xC(S)NR^yR^z$, —$C(O)NR^yR^z$, —$C(S)NR^yR^z$, wherein $R^x$, $R^y$ and $R^z$ are independently selected from hydrogen or $C_{1-6}$ alkyl.

In another preferred embodiment of the invention, [$Y^+$] represents a saturated heterocyclic cation selected from cyclic ammonium, 1,4-diazabicyclo[2.2.2]octanium, morpholinium, cyclic phosphonium, piperazinium, piperidinium, quinuclidinium, and cyclic sulfonium.

Preferably, [$Y^+$] represents a saturated heterocyclic cation having the formula:

wherein: $R^a$, $R^b$, $R^c$, $R^d$, $R^e$ and $R^f$, are as defined above.

Preferably, at least one of $R^a$, $R^b$, $R^c$, $R^d$, $R^e$ and $R^f$ is $C_{1-3}$ alkyl group substituted with —$CO_2R^x$, —$C(O)NR^yR^z$, wherein $R^x$, $R^y$ and $R^z$ are each independently selected from $C_{3-6}$ alkyl.

More preferably, at least one of $R^a$, $R^b$, $R^c$, $R^d$, $R^e$ and $R^f$ represents a group selected from:

wherein $R^y = R^z$, and wherein $R^x$, $R^y$ and $R^z$ are each selected from $C_{3-6}$ alkyl, preferably $C_4$ alkyl, for example i-Bu.

Yet more preferably, at least one of $R^a$, $R^b$, $R^c$, $R^d$, $R^e$ and $R^f$ represents a group selected from:

wherein $R^y = R^z$, and wherein $R^y$ and $R^z$ are selected from $C_{3-6}$ alkyl, preferably $C_4$ alkyl, for example i-Bu.

In preferred embodiments, one of $R^a$, $R^b$, $R^c$, $R^d$, $R^e$ and $R^f$ is a substituted $C_{1-5}$ alkyl group, and the remainder of $R^a$, $R^b$, $R^c$, $R^d$, $R^e$ and $R^f$ are independently selected from H and unsubstituted $C_{1-5}$ alkyl groups, preferably the remainder of $R^a$, $R^b$, $R^c$, $R^d$, $R^e$ and $R^f$ are H.

Preferably, [Y$^+$] represents a cyclic cation selected from:

more preferably [Y$^+$] represents the cyclic cation:

preferably wherein $R^f$ is a substituted $C_{1-5}$ alkyl group, and the remainder of $R^a$, $R^b$, $R^c$, $R^d$, $R^e$ and $R^f$ are independently selected from H and unsubstituted $C_{1-5}$alkyl groups.

In preferred embodiments, $L_1$ represents a linking group selected from $C_{1-10}$ alkanediyl and $C_{1-10}$ alkenediyl groups, more preferably selected from $C_{1-5}$alkanediyl and $C_{2-5}$ alkenediyl groups, and most preferably selected from $C_{1-5}$ alkanediyl groups, for example a linking group selected from —CH$_2$—, —C$_2$H$_4$— and —C$_3$H$_6$—.

In preferred embodiments, each $L_2$ represents a linking group independently selected from $C_{1-2}$ alkanediyl and $C_2$ alkenediyl groups, preferably selected from $C_{1-2}$ alkanediyl groups, for example independently selected from —CH$_2$— and —C$_2$H$_4$—.

Each EDG may be any suitable electron donating group able to form a coordinate bond with a rare earth metal to form a metal-ligand complex.

Preferably, each EDG represents an electron donating group independently selected from —CO$_2$R$^x$, —OC(O)R$^x$, —CS$_2$R$^x$, —SC(S)R$^x$, —S(O)OR$^x$, —OS(O)R$^x$, —NR$^x$C(O)NR$^y$R$^z$, —NR$^x$C(O)OR$^y$, —OC(O)NR$^y$R$^z$, —NR$^x$C(S) OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, wherein R$^x$, R$^y$ and R$^z$ are independently selected from H or C$_{1-6}$ alkyl. More preferably, each EDG represents an electron donating group independently selected from —CO$_2$R$^x$ and —C(O)NR$^y$R$^z$, wherein R$^x$, R$^y$ and R$^z$ are each independently selected from C$_{3-6}$ alkyl.

In preferred embodiments, each -L$_2$-EDG represents an electron donating group independently selected from:

wherein R$^y$=R$^z$, and wherein R$^x$, R$^y$ and R$^z$ are each selected from C$_{3-6}$ alkyl, preferably C$_4$ alkyl, for example i-Bu.

More preferably, each -L$_2$-EDG represents an electron donating group independently selected from:

wherein R$^y$=R$^z$, and wherein R$^y$ and R$^z$ are selected from C$_{3-6}$ alkyl, preferably C$_4$ alkyl, for example i-Bu.

It will be appreciated that, as set out previously, the extraction of rare earth metals is provided by the specific functionality of the cation of the ionic liquid. Thus, any suitable anionic species [X$^-$] may be used as part of the ionic liquid used in the method of the present invention.

Preferably, [X$^-$] represents one or more anionic species selected from: hydroxides, halides, perhalides, pseudohalides, sulphates, sulphites, sulfonates, sulfonimides, phosphates, phosphites, phosphonates, methides, borates, carboxylates, azolates, carbonates, carbamates, thiophosphates, thiocarboxylates, thiocarbamates, thiocarbonates, xanthates, thiosulfonates, thiosulfates, nitrate, nitrite, tetrafluoroborate, hexafluorophosphate and perchlorate, halometallates, amino acids, borates, polyfluoroalkoxyaluminates.

For example, [X$^-$] preferably represents one or more anionic species selected from:
a) a halide anion selected from: F$^-$, Cl$^-$, Br$^-$, I$^-$;
b) a perhalide anion selected from: [I$_3$]$^-$, [I$_2$Br]$^-$, [IBr$_2$]$^-$, [Br$_3$]$^-$, [Br$_2$Cl]$^-$, [BrCl$_2$]$^-$, [ICl$_2$]$^-$, [I$_2$Cl]$^-$, [Cl$_3$]$^-$;
c) a pseudohalide anion selected from: [N$_3$]$^-$, [NCS]$^-$, [NCSe]$^-$, [NCO]$^-$, [CN]$^-$;
d) a sulphate anion selected from: [HSO$_4$]$^-$, [SO$_4$]$^{2-}$, [R$^2$OSO$_2$O]$^-$;
e) a sulphite anion selected from: [HSO$_3$]$^-$, [SO$_3$]$^{2-}$, [R$^2$OSO$_2$]$^-$;
f) a sulfonate anion selected from: [R$^1$SO$_2$O]$^-$;
g) a sulfonimide anion selected from: [(R$^1$SO$_2$)$_2$N]$^-$;
h) a phosphate anion selected from: [H$_2$PO$_4$]$^-$, [HPO$_4$]$^{2-}$, [PO$_4$]$^{3-}$, [R$^2$OPO$_3$]$^{2-}$, [(R$^2$O)$_2$PO$_2$]$^-$;
i) a phosphite anion selected from: [H$_2$PO$_3$]$^-$, [HPO$_3$]$^{2-}$, [R$^2$OPO$_2$]$^{2-}$, [(R$^2$O)$_2$PO]$^-$;
j) a phosphonate anion selected from: [R$^1$PO$_3$]$^{2-}$, [R$^1$P(O)(OR$^2$)O]$^-$;
k) a methide anion selected from: [(R$^1$SO$_2$)$_3$C]$^-$;

l) a borate anion selected from: [bisoxalatoborate], [bismalonatoborate]tetrakis[3,5-bis(trifluoromethyl)phenyl]borate, tetrakis(pentafluorophenyl)borate;

m) a carboxylate anion selected from: $[R^2CO_2]^-$;

n) an azolate anion selected from: [3,5-dinitro-1,2,4-triazolate], [4-nitro-1,2,3-triazolate], [2,4-dinitroimidazolate], [4,5-dinitroimidazolate], [4,5-dicyano-imidazolate], [4-nitroimidazolate], [tetrazolate];

o) a sulfur-containing anion selected from: thiocarbonates (e.g. $[R^2OCS_2]^-$, thiocarbamates (e.g. $[R^2{}_2NCS_2]^-$), thiocarboxylates (e.g. $[R^1CS_2]^-$), thiophosphates (e.g. $[(R^2O)_2PS_2]^-$), thiosulfonates (e.g. $[RS(O)_2S]^-$), thiosulfates (e.g. $[ROS(O)_2S]^-$);

p) a nitrate ($[NO_3]^-$) or nitrite ($[NO_2]^-$) anion;

q) a tetrafluoroborate ($[BF_4^-]$), hexafluorophosphate ($[PF_6^-]$), hexfluoroantimonate ($[SbF_6^-]$) or perchlorate ($[ClO_4^-]$) anion;

r) a carbonate anion selected from $[CO_3]^{2-}$, $[HCO_3]^-$, $[R^2CO_3]^-$; preferably $[MeCO_3]^-$;

s) polyfluoroalkoxyaluminate anions selected from $[Al(OR^F)_4^-]$, wherein $R^F$ is selected from $C_{1-6}$ alkyl substituted by one or more fluoro groups;

where: $R^1$ and $R^2$ are independently selected from the group consisting of $C_1$-$C_{10}$ alkyl, $C_6$ aryl, $C_1$-$C_{10}$ alkyl($C_6$)aryl and $C_6$ aryl($C_1$-$C_{10}$)alkyl each of which may be substituted by one or more groups selected from: fluoro, chloro, bromo, iodo, $C_1$ to $C_6$ alkoxy, $C_2$ to $C_{12}$ alkoxyalkoxy, $C_3$ to $C_8$ cycloalkyl, $C_6$ to $C_{10}$ aryl, $C_7$ to $C_{10}$ alkaryl, $C_7$ to $C_{10}$ aralkyl, —CN, —OH, —SH, —NO$_2$, —CO$_2$R$^x$, —OC(O)R$^x$, —C(O)R$^x$, —C(S)R$^x$, —CS$_2$R$^x$, —SC(S)R$^x$, —S(O)(C$_1$ to C$_6$)alkyl, —S(O)O(C$_1$ to C$_6$)alkyl, —OS(O)(C$_1$ to C$_6$)alkyl, —S(C$_1$ to C$_6$)alkyl, —S—S(C$_1$ to C$_6$ alkyl), —NR$^x$C(O)NR$^y$R$^z$, —NR$^x$C(O)OR$^y$, —OC(O)NR$^y$R$^z$, —NR$^x$C(S)O R$^y$, —OC(S)NR$^y$R$^z$, —NR$^x$C(S) SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein R$^x$, R$^y$ and R$^z$ are independently selected from hydrogen or $C_1$ to $C_6$ alkyl, wherein $R^1$ may also be fluorine, chlorine, bromine or iodine.

While [X$^-$] may be any suitable anion, it is preferred that [X$^-$] represents a non-coordinating anion. The term "non-coordinating anion" used herein, which is common in the field of ionic liquids and metal coordination chemistry, is intended to mean an anion that does not coordinate with a metal atom or ion, or does so only weakly. Typically, non-coordinating anions have their charge dispersed over several atoms in the molecule which significantly limits their coordinating capacity. This limits the effect interference of the anion with the selective coordination of the cation [Cat$^+$] with the rare earth metal.

Thus, more preferably, [X$^-$] represents one or more non-coordinating anionic species selected from: bistriflimide, triflate, tosylate, perchlorate, $[Al(OC(CF_3)_3)_4^-]$, tetrakis[3,5-bis(trifluoromethyl) phenyl]borate, tetrakis(pentafluorophenyl)borate, tetrafluoroborate, hexfluoroantimonate and hexafluorophosphate anions; and most preferably from bistriflimide and triflate anions.

In some preferred embodiments, [Cat$^+$] represents one or more ionic species having the structure:

where: [Z$^+$] represents a group selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups.

It will be understood that the composition may comprise the ionic liquid as defined above in combination with a diluent. Typically, a diluent may be used in order to decrease the viscosity of the composition where the ionic liquid has a high viscosity, which limits its practical use in liquid-liquid extraction. A diluent may also be used to save costs where the diluent is cheaper to produce than the ionic liquid. It will be understood that any diluent added to the composition will be sufficiently hydrophobic so as to allow the separation of the composition and the acidic solution of the rare earth metal into an aqueous and non-aqueous phase. In some embodiments, the diluent may enhance the hydrophobicity of the composition.

Thus, in preferred embodiments, the composition further comprises a lower viscosity ionic liquid. The term "lower viscosity ionic liquid" will be understood to mean that this ionic liquid has a lower viscosity than the ionic liquid extractant described previously. As mentioned, it will be understood that the lower viscosity ionic liquid will be sufficiently hydrophobic so as to allow the separation of the composition and the acidic solution of the rare earth metal into an aqueous and non-aqueous phase. It will also be appreciated that the hydrophobicity may be provided by either of the cation or anion of the lower viscosity ionic liquid, or by both.

By the use of an ionic liquid as a diluent, the decreased volatility and flammability offered by the ionic liquid extractant may be maintained to give a potentially safer and more environmentally friendly rare earth metal extraction process.

In preferred embodiments, the cation of the lower viscosity ionic liquid is selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups.

Preferably the cation of the lower viscosity ionic liquid is selected from phosphonium, imidazolium and ammonium groups.

In some preferred embodiments, the cation of the lower viscosity ionic liquid is selected from:

wherein: $R^3$, $R^4$, $R^5$ and $R^6$ are each independently selected from optionally substituted $C_{1-20}$ alkyl, $C_{3-8}$ cycloalkyl and $C_{6-10}$ aryl groups.

In more preferred embodiments, the cation of the lower viscosity ionic liquid is $[P(R^3)(R^4)(R^5)(R^6)]^+$, wherein $R^3$, $R^4$, $R^5$ are selected from $C_{1-10}$ alkyl, preferably $C_{2-6}$ alkyl, and $R^6$ is selected from $C_{4-20}$ alkyl, preferably $C_{8-14}$ alkyl. For example, the cation of the lower viscosity ionic liquid may be selected from triethyloctyl phosphonium ($P_{222(8)}^+$), tributyloctyl phosphonium ($P_{444(8)}^+$), trihexyloctyl phosphonium ($P_{666(8)}^+$), trihexyldecyl phosphonium ($P_{666(10)}^+$), and trihexyltetradecyl phosphonium ($P_{666(14)}^+$).

In other more preferred embodiments, the cation of the lower viscosity ionic liquid is $[N(R^3)(R^4)(R^5)(R^6)]^+$, wherein $R^3$, $R^4$, $R^5$ are selected from $C_{4-14}$ alkyl, preferably $C_{6-10}$ alkyl, and $R^6$ is selected from $C_{1-4}$ alkyl, preferably $C_{1-2}$ alkyl. For example, the cation of the lower viscosity ionic liquid may be selected from trioctylmethyl ammonium, tris(2-ethylhexyl) methyl ammonium, and tetrabutyl ammonium.

In other preferred embodiments, the cation of the lower viscosity ionic liquid is selected from imidazolium cations substituted with one or more $C_{1-20}$ alkyl, $C_{3-8}$ cycloalkyl and $C_{6-10}$ aryl groups, preferably substituted with two $C_{1-10}$ alkyl groups, more preferably substituted with one methyl group and one $C_{1-10}$ alkyl group. For example, the cation of the lower viscosity ionic liquid may be selected from 1-butyl-3-methyl imidazolium, 1-hexyl-3-methyl imidazolium and 1-octyl-3-methyl imidazolium.

It will be understood that any suitable anionic group may be used as the anion of the lower viscosity ionic liquid. Preferably, the anion of the lower viscosity ionic liquid is as described previously in relation to the anionic group [X]. For example, it is most preferred that the anion of the lower viscosity ionic liquid is a non-coordinating anion as described previously. It will be appreciated that there may be an excess of anions from the lower viscosity ionic liquid in comparison to the ionic liquid extractant. Therefore, it is especially preferred that the anion of the lower viscosity ionic liquid is a non-coordinating anion.

For this reason, it is preferable to limit the total amount of halide or pseudohalide anions in the composition. For example, in preferred embodiments the composition comprises less than 25% halide or pseudohalide anions as a proportion of the total anions, preferably less than 20%, more preferably less than 15%, most preferably less than 10%, for example less than 5%. In some embodiments, the composition is substantially free of halide or pseudohalide anions.

The composition may alternatively or additionally further comprise one or more non-ionic liquid diluents. For example, in some preferred embodiments the composition further comprises one or more organic solvents. It will be understood that suitable organic solvents will include hydrophobic and non-coordinating solvents. The term "non-coordinating solvent" used herein, which is common in the field of metal coordination chemistry, is intended to mean a solvent that does not coordinate with metal atoms or ions, or does so only weakly.

Suitable organic solvents include but are not limited to hydrocarbon solvents such as $C_{1-20}$ alkanes, alkenes or cycloalkanes, aromatic solvents such as toluene or benzene, $C_{6+}$ alcohols such as n-hexanol, etheric solvents such as diethyl ether, dipropyl ether, dibutyl ether and methyl-t-butyl ether, or halogenated solvents such as tetrachloromethane, tetrachloroethane, chloroform, dichloromethane, chlorobenzene, or fluorobenzene. Preferably the organic solvent is a hydrocarbon solvent.

The ionic liquid may be present in the composition in any concentration suitable for extracting rare earth metals and it will be appreciated that this concentration will vary depending on the particular application and pH. In particular, it will be appreciated that for the separation of rare earth metals a competitive separation is desirable. For example the concentration of the ionic liquid should be low enough to avoid the extraction of all rare earth metals present. Therefore, the concentration of the ionic liquid will typically depend on the concentration of rare earth metals to be extracted and the pH at which the separation is conducted. In some preferred embodiments, the ionic liquid is present in the composition in a concentration of at least 0.001 M, preferably from 0.005 M to 0.01 M.

In other embodiments, the composition may consist essentially of the ionic liquid.

It will be appreciated that the concentration of the ionic liquid in the composition may be varied in order to achieve a particular target viscosity for the composition. It will also be appreciated that the character of the lower viscosity ionic liquid or other diluent may be varied in order to obtain a particular viscosity level.

In preferred embodiments, the viscosity of the composition is in the range of from 50 to 500 mPa·s at 298K, when the composition comprises a solution of the ionic liquid in a lower viscosity ionic liquid. When the ionic liquid is in a solution of an organic solvent, it will be appreciated that the composition will likely have a lower viscosity, for example, less than 50 mPa·s. Viscosity may be measured by any suitable method, for example viscosity may be measured using a rotating disk viscometer with variable temperature.

In some embodiments, the acidic solution is obtainable by leaching the rare earth metal from its source using an acid, for example a mineral acid such as hydrochloric, nitric, perchloric or sulfuric acid, typically hydrochloric or nitric acid. Preferably, the source of the rare earth metal is a mineral or a waste material. However, it will be appreciated that the acidic solution of the rare earth metal or mixture of rare earth metals may be obtained in any suitable way from any rare earth metal source.

The concentration of rare earth metals in the acidic solution is typically from 60 ppm to 2000 ppm. Nonetheless, it will be appreciated that any suitable concentration of rare earth metals in the acid solution may be used.

Typically, rare earth metals are obtained from rare earth ores, which are mined and processed by a variety of methods depending on the particular ore. Such processes are well known in the art. Usually, following mining such processes may include steps such as grinding, roasting to remove carbonates, chemical processing (e.g alkali/hydroxide treatment), and ultimately leaching with acid to obtain an aqueous acidic solution containing a mixture of rare earth metals.

Examples of rare earth metal bearing minerals contained in rare earth ores are aeschynite, allanite, apatite, bastnäsite, brannerite, britholite, eudialyte, euxenite, fergusonite, gadolinite, kainosite, loparite, monazite, parisite, perovskite, pyrochlore, xenotime, yttrocerite, huanghoite, cebaite, florencite, synchysite, samarskite, and knopite.

Rare earth metals may also increasingly be obtained from recycled materials. As global demand for rare earth metals grows, it is increasingly attractive to obtain earth metals from recycled waste materials, particularly in countries with a lack of minable rare earth ore deposits. Rare earth waste materials may be obtained from various sources, for example direct recycling of rare earth scrap/residues from pre-consumer manufacturing, "urban mining" of rare earth containing end of life products, or landfill mining of urban and industrial waste containing rare earths. As rare earth metals are increasingly being used in consumer products, the amount of rare earth metals that can be obtained from such waste materials is also growing.

Waste materials that may contain rare earth metals include, magnetic swarf and rejected magnets, rare earth containing residues from metal production/recycling (e.g. postsmelter and electric arc furnace residues or industrial residues such as phosphogypsum and red mud), phosphors such as those in fluorescent lamps, LEDs, LCD backlights, plasma screens and cathode ray tubes, permanent magnets (e.g. NdFeB) such as those used in automobiles, mobile phones, hard disk drives, computers and peripherals, electronic kitchen utensils, hand held tools, electric shavers, industrial electric motors, electric bicycles, electric vehicle and hybrid vehicle motors, wind turbine generators, nickel-metal hydride batteries such as are used for rechargeable batteries and electric and hybrid vehicle batteries, glass polishing powders, fluid cracking catalysts and optical glass. Major end-of-life waste material sources of rare earths in terms of value are permanent magnets, nickel-metal hydride batteries and lamp phosphors, as well as scrap in the form of magnetic swarf waste.

Rare earth metals will usually be extracted from waste materials by leaching with mineral acids and optionally further processing to remove impurities such as transition metals. This results in an acidic solution of the rare earth metals, which may be used as a source for separation and purification of the individual rare earth metals.

Thus, it is an advantage of the present invention that rare earth metals may be extracted with high selectivity and extractability directly from an acidic solution of the rare earth metal, which may be conveniently obtained from the extraction process of an ore or a waste material.

In a further aspect of the present invention, there is provided an ionic liquid ($[Cat^+][X^-]$) substantially as described previously herein.

In a further aspect of the present invention, there is provided a composition substantially as described previously herein.

In some preferred embodiments, the composition further comprises a rare earth metal. It will be appreciated that the composition comprising a rare earth metal may be a valuable resource in itself and it will not always be desirable to separate the rare earth metal, for example by stripping with acid.

For example, the composition further comprising a rare earth metal may be used for electrodeposition of the rare earth metal or precipitation of one or more rare earth metals (e.g. with oxalic acid).

Electrodeposition of rare earth metals from ionic liquids and precipitation of rare earth metals from solution are well known in the art any may be performed in any suitable way, as will be appreciated by one skilled in the art.

In a further aspect of the present invention, there is provided the use of the composition further comprising a rare earth metal for electrodeposition of a rare earth metal.

In a further aspect of the present invention, there is provided the use of the composition further comprising a rare earth metal for precipitation of a rare earth metal.

In a further aspect of the present invention, there is provided a method for preparing an ionic liquid as defined in Claim 59, said method comprising reacting:

where: LG represents a leaving group.

A "leaving group" as used herein will be understood to mean a group that may be displaced from a molecule by reaction with a nucleophilic centre, in particular a leaving group will depart with a pair of electrons in heterolytic bond cleavage. A leaving group is usually one that is able to stabilize the additional electron density that results from bond heterolysis. Such groups are well-known in the field of chemistry.

It will be understood that the group [Z] may be any group that is able to displace the leaving group to form a $[Z^+]$ cation as defined previously herein.

It will be appreciated that a leaving group as defined herein will be such that the primary amine coupled by $L_1$ to [Z] may displace the leaving group to form a bond between the nitrogen and an $L_2$ group, and such that the group [Z] can displace the leaving group to form a bond between [Z] and an $L_2$ group.

Leaving groups may, for example, include a group selected from dinitrogen, dialkyl ethers, perfluoroalkylsulfonates such as triflate, tosylate or mesylate, halogens such as Cl, Br and I, water, alcohols, nitrate, phosphate, thioethers and amines. Preferably, the leaving group LG is selected from halides, more preferably the leaving group LG is Cl.

Such substitution reactions as described herein are well-known in the art and could be performed by a skilled person without difficulty.

By preparing an ionic liquid by this method, an ionic liquid having advantageous rare earth metal extraction properties may be conveniently synthesised in a single step, reducing the increased costs associated with multiple step syntheses.

In a further aspect of the present invention, there is provided the use of the ionic liquid or the composition further comprising a rare earth metal as described herein for extracting rare earth metals. Preferably, the ionic liquid or the composition is used to preferentially extract a first rare earth metal from a solution which comprises a first and a second rare earth metal.

The present invention will now be illustrated by way of the following examples and with reference to the following figures in which.

EXAMPLES

Example 1: Synthesis of Ionic Liquid

General Procedure for the Synthesis of an Ionic Liquid According to Embodiments of the Invention A reaction mixture comprising 3 moles of an N,N-dialkyl-2-chloroacetamide and a substrate having the structure H$_2$N-L$_1$-[Z] were stirred in a halogenated solvent (e.g. CHC$_3$, CH$_2$Cl$_2$, etc.) or an aromatic solvent (e.g. toluene, xylene, etc.) at 60 to 70° C. for 7 to 15 days. After cooling, the solid was filtered off and the organic phase was repeatedly washed with 0.1 to 0.2 M HCl until the aqueous phase showed milder acidity (pH>2). The organic phase was then washed with 0.1 M Na$_2$CO$_3$ (2-3 washes) and finally was washed with deionized water until the aqueous phase showed a neutral pH. The solvent was removed under high vacuum to give the ionic liquid product (with a chloride anion) as a highly viscous liquid. This ionic liquid could be used as it was or the chloride anion could be exchanged with different anions (e.g. bistriflimide, triflate, hexafluorophosphate etc.) using conventional metathesis routes, for example, by reacting with an alkali metal salt of the desired anion with the ionic liquid in an organic solvent.
Synthesis of an Imidazolium Ionic Liquid

[MAIL$^+$]Cl$^-$ 1-(3-Aminopropyl)-imidazole (0.05 mol) was added to of N,N-diisobutyl-2-chloroacetamide (0.15 mol) in a 500 ml three necked round bottom flask. Triethylamine (0.11 moles) was then added along with chloroform (200 ml). The reaction was stirred for 6 hours at room temperature and then stirred at 60 to 70° C. for 7 days. The reaction mixture was then cooled and after filtration it was successively washed with 0.1 M HCl, 0.1 M Na$_2$CO$_3$ and deionized water (as described in general procedure). The solvent was removed from the neutralised organic phase at 8 mbar (6 mm Hg) and finally at 60° C. and 0.067 mbar (0.05 mmHg). The ionic liquid [MAIL$^+$]Cl$^-$ was recovered as a highly viscous yellow liquid.

Ionic liquid [MAIL$^+$]Cl$^-$ (0.025 mol) was dissolved in chloroform and lithium bis-(trifluoromethane) sulfonamide (LiNTf$_2$) (0.03 mol) was added. The reaction mixture was stirred for 1 hour and then the organic phase was repeatedly washed with deionized water. Finally the solvent was removed from the organic phase under vacuum (0.13 mbar, 0.1 mm Hg) at 65° C. to yield the bistriflimide anion form of the ionic liquid ([MAIL$^+$][NTf$_2^-$]).

Example 2: Liquid-Liquid Extraction of Rare Earth Metals Using [MAIL$^+$][NTf$_2^-$]

General Procedure for Extraction of Rare Earth Metals

Equal volumes (2 to 5 ml) of the ionic liquid extractant ([MAIL$^+$][NTf$_2^-$] in [P$_{666(14)}^+$][NTf$_2^-$]) and an acidic aqueous feed solution containing rare earth metals in HCl were equilibrated for 15-30 minutes on a wrist action shaker. The phases were centrifuged and the aqueous phase was analysed for rare earth metal content using Inductively Coupled Plasma Optical Emission Spectroscopy (ICP-OES), though it will be appreciated that any suitable analysis technique may be used. The proportion of the rare earth metals extracted into the ionic liquid (organic) phase was determined through mass balance using the ICP-OES measurement.

The distribution ratio of an individual rare earth metal was determined as the ratio of its concentration in the ionic liquid phase to that of it in the aqueous phase (raffinate). $D_M = [M]_{IL}/[M]_{Aq}$, where IL represents ionic liquid phase and Aq represents the aqueous phase (raffinate).

The separation factor (SF) with respect to an individual rare earth metal pair is expressed as the ratio of the distribution ratio of a first rare earth metal with the distribution ratio of a second rare earth metal. For example, the separation factor of dysprosium with respect to neodymium=$D_{Dy}/D_{Nd}$. It will be appreciated that separation factors estimated from independently obtained distribution ratios will be lower than the actual separation factors, obtained during the separation of mixtures of rare earth metals during a competitive separation (as exemplified below).

Figure 1:
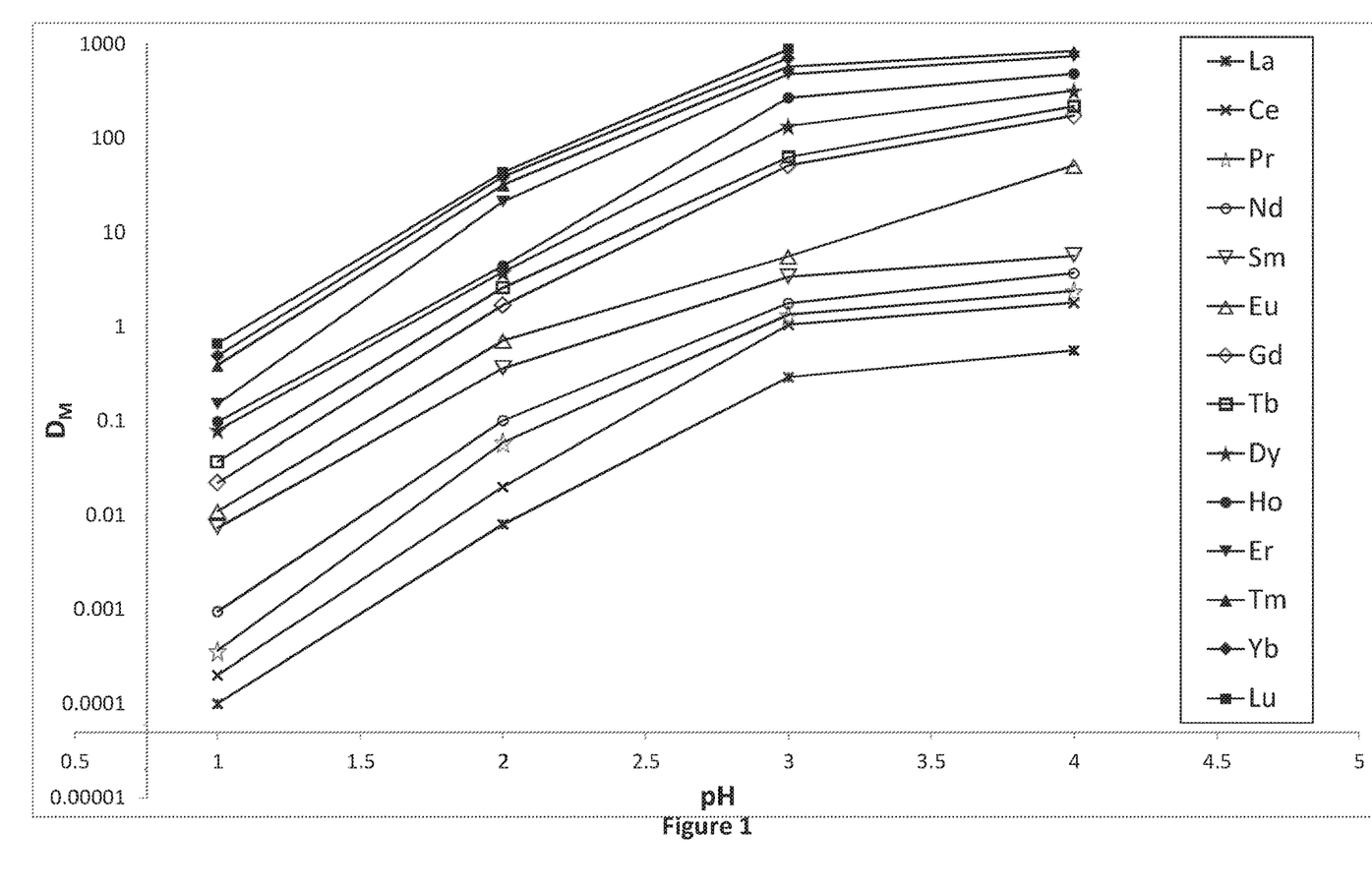
FIG. 1 is a graph showing the distribution factors for the extraction of a selection of rare earth metals according to an embodiment of the present invention.
Figure 2:
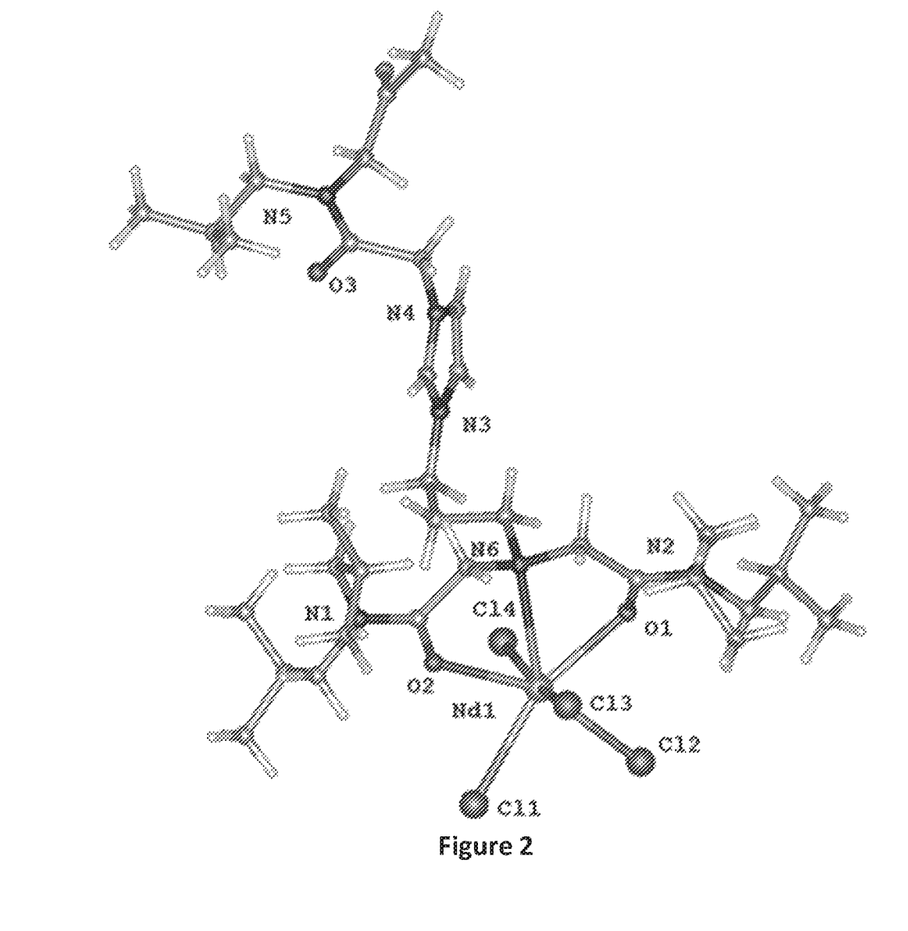
FIG. 2 shows the crystal structure of the [MAIL]$^+$ cation coordinating to Nd after extraction from an acidic (HCl) solution containing NdCl$_3$.6H$_2$O.

Distribution ratios for individual rare earth metals were obtained in separate extractions according to the general procedure above, using 0.0075 M [MAIL$^+$][NTf$_2^-$] in [P$_{666(14)}^+$][NTf$_2^-$] and a 200 mg/l (ppm) HCl solution of the relevant rare earth metal chloride (where 200 ppm refers to the concentration of the elemental metal in the solution). FIG. 1 shows a plot of the distribution ratios for each rare earth metal as a function of pH, showing that the ionic liquid according to the present invention may be used to extract rare earth metals across a range of pH values.
Separation of Dy and Nd An aqueous HCl solution containing DyCl$_3$.6H$_2$O (60 mg/l (ppm) Dy) and NdCl$_3$.6H$_2$O (1400 mg/l (ppm) Nd) at pH 3 was extracted with the ionic liquid extractant (0.005 M [MAIL$^+$][NTf$_2^-$] in [P$_{666(14)}^+$][NTf$_2^-$]) according to the general procedure above. A single contact (extraction) gave $D_{Dy}$=13.45, $D_{Nd}$=0.0124, giving a SF$_{Dy-Nd}$ of 1085.

This separation factor (1085) is considerably higher than the separation factors obtained for Dy/Nd separation by the systems in the prior art shown in Table 1 (maximum 239).
Separation of Eu and La An aqueous HCl solution containing EuCl$_3$.6H$_2$O (65 mg/l (ppm) Eu) and LaCl$_3$.7H$_2$O (470 mg/l (ppm) La) at pH 3 was extracted with the ionic liquid extractant (0.005 M [MAIL$^+$][NTf$_2^-$] in [P$_{666(14)}^+$][NTf$_2^-$]) according to the general procedure above. A single contact (extraction) gave D$_{Eu}$=9.3, D$_{La}$=0.044, giving a SF$_{Eu-La}$ of 211.

Separation of Tb and Ce

An aqueous HCl solution containing TbCl$_3$.6H$_2$O (530 mg/l (ppm) Tb) and CeCl$_3$.6H$_2$O (950 mg/l (ppm) Ce) at pH 3 was extracted with the ionic liquid extractant (0.0075 M [MAIL$^+$][NTf$_2^-$] in [P$_{666(14)}^+$][NTf$_2^-$]) according to the general procedure above. A single contact (extraction) gave D$_{Tb}$=11.2, D$_{Ce}$=0.068, giving a SF$_{Tb-Ce}$ of 162.

Example 3: Stripping of Rare Earth Metals from [MAIL$^+$][NTf$_2^-$]

Dy(III) (200 ppm) was stripped from an organic phase at pH 3 comprising [MAIL$^+$][NTf$_2^-$] in [P$_{666(14)}^+$][NTf$_2^-$] (0.005 M) in 2 successive contacts. The organic phase was contacted with an equal volume of an aqueous HCl solution (0.2 M) and was equilibrated for 15-30 minutes on a wrist action shaker. 140 ppm of Dy(III) was stripped in the first contact and 55 ppm was stripped in the second contact.

Similarly, from observation of the distribution ratios in FIG. 1, it is clear that heavy rare earth metals such as Tm, Yb and Lu have significantly reduced distribution factors with increasing acidity. Thus, it is also expected that heavy rare earth metals may be stripped from the ionic liquid of the present invention at relatively high pH values.

The above examples show that a large increase in the separation factors between key rare earth metal pairs may be obtained by use of an ionic liquid according to the present invention (e.g. Nd/Dy: Nd—Dy magnet, Eu/La: white lamp phosphor, Tb/Ce: green lamp phosphor). The rare earth metals may also be advantageously stripped from the ionic liquid at relatively high pH compared to prior art systems.

Without wishing to be bound by any particular theory, it is believed that a more pronounced increase in distribution ratios is observed for heavier rare earth metals than lighter rare earth metals as a result of increased formation of the more hydrophobic doubly coordinated rare earth metal species M.([MAIL$^+$][NTf$_2^-$])$_2$ over the singly coordinated species M.([MAIL$^+$][NTf$_2^-$]). It is believed that the more hydrophobic species will be more easily extracted into the organic phase during separation, leading to increased distribution ratios.

Nuclear magnetic resonance, infra-red and mass spectrometry studies have shown that the doubly coordinated species is more abundant in solutions of Lu and the ionic liquid compared to solutions of La and the ionic liquid, highlighting the differentiation between the heavy and light rare earth metals achieved by the ionic liquid of the present invention.

Furthermore, optimised geometries of the complexes LaCl$_3$.([MAIL$^+$][Cl$^-$])$_2$ and LuCl$_3$.([MAIL$^+$][Cl$^-$])$_2$ show that the distance between the tertiary central nitrogen of the ionic liquid cation and the metal is much longer in the case of La (~2.9 Å, non-bonding) than in the case of Lu (~2.6 Å, bonding), which also supports the weaker bonding of the ionic liquid to lighter rare earth metals. At the same time, the electron donating groups, in this case amides, linked to the nitrogen atom bond to the metal in a very similar way in both cases. This result shows that the central motif of the ionic liquid cation having a tertiary nitrogen donor is important for the differentiation obtained between the heavier and lighter rare earth metals and the improved selectivity that results therefrom.

The invention claimed is:

1. A method for extracting a rare earth metal from a mixture comprising one or more rare earth metals, said method comprising contacting an acidic solution of the rare earth metal with a composition which comprises an ionic liquid to form an aqueous phase and a non-aqueous phase into which the rare earth metal has been selectively extracted, wherein the ionic liquid has the formula:

in which:

[Cat$^+$] represents a cationic species having the structure:

where: [Y$^+$] comprises ammonium, benzimidazolium, benzofuranium, benzothiophenium, benzotriazolium, borolium, cinnolinium, diazabicyclodecenium, diazabicyclononenium, 1,4-diazabicyclo [2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium or uronium; each EDG represents an electron donating group;

L$_1$ is selected from C$_{1-10}$ alkanediyl, C$_{2-10}$ alkenediyl, C$_{1-10}$ dialkanylether or C$_{1-10}$ dialkanylketone groups;

each L$_2$ is independently selected from C$_{1-2}$ alkanediyl, C$_2$ alkenediyl, C$_{1-2}$ dialkanylether or C$_{1-2}$ dialkanylketone; and

[X$^-$] represents an anionic species.

2. The method of claim 1, wherein the method comprises recovering the rare earth metal from the non-aqueous phase by stripping with an acidic stripping solution comprising at least one of: an aqueous hydrochloric acid, nitric acid solution or an acidic stripping solution having a pH of 0 or higher.

3. The method of claim 1, wherein the method comprises extracting a rare earth metal from a mixture of two or more rare earth metals.

4. The method of claim 1, wherein the acidic solution comprises a first and a second rare earth metal, and the method comprises:

(a) partitioning the first rare earth metal into the non-aqueous phase and separating the non-aqueous phase from the acidic solution; and (b) contacting the acidic solution depleted of the first rare earth metal with the composition which comprises an ionic liquid, and recovering the second rare earth metal therefrom.

5. The method of claim 4, wherein at least one of: the first rare earth metal is dysprosium and the second rare earth metal is neodymium; the first rare earth metal is lanthanum and the second rare earth metal is europium; or the acidic solution has a pH of less than 3.5 in step (a), and the acidic solution has a pH of greater than 3.5 in step (b).

6. The method of claim 1, wherein at least one of: the acidic solution from which the rare earth metal is extracted has a pH of from 2 to 4; or prior to contacting the composition with the acidic solution of the rare earth metal the composition is equilibrated with an acidic solution having the same pH as the acidic solution of the rare earth metal.

7. The method of claim 1, wherein the composition is added to the acidic solution in a volume ratio of from 0.5:1 to 2:1.

8. The method of claim 1, wherein the method comprises contacting the acidic solution of the rare earth metal and the composition for from 10 to 40 minutes, and/or wherein the method comprises contacting and physically mixing the acidic solution of the rare earth metal and the composition.

9. The method of claim 1, wherein when the nitrogen linking $L_1$ to each $L_2$ and one of the EDG both coordinate to a metal, the ring formed by the nitrogen, $L_2$, the EDG and the metal is a 5 or 6 membered ring.

10. The method of claim 1, wherein [Y$^+$] represents an acyclic cation selected from at least one of:

wherein: $R^a$, $R^b$ and $R^c$ are each independently selected from optionally substituted $C_{1-30}$ alkyl, $C_{3-8}$ cycloalkyl and $C_{6-10}$ aryl groups;

a cyclic cation selected from:

wherein: $R^a$, $R^b$, $R^c$, $R^d$, $R^e$ and $R^f$ are each independently selected from: hydrogen and optionally substituted $C_{1-30}$ alkyl, $C_{3-8}$ cycloalkyl and $C_{6-10}$ aryl groups, or any two of $R^a$, $R^b$, $R^c$, $R^d$ and $R^e$ attached to adjacent carbon atoms form an optionally substituted methylene chain —(CH$_2$)$_q$— where q is from 3 to 6;

a saturated heterocyclic cation selected from cyclic ammonium, 1,4-diazabicyclo[2.2.2]octanium, morpholinium, cyclic phosphonium, piperazinium, piperidinium, quinuclidinium, and cyclic sulfonium;

a saturated heterocyclic cation having the formula:

wherein: $R^a$, $R^b$, $R^c$, $R^d$, $R^e$ and $R^f$, are each independently selected from: hydrogen and optionally substituted $C_{1-30}$ alkyl, $C_{3-8}$ cycloalkyl and $C_{6-10}$ aryl groups, or any two of $R^a$, $R^b$, $R^c$, $R^d$ and $R^e$ attached to adjacent carbon atoms form an optionally substituted methylene chain —(CH$_2$)$_q$— where q is from 3 to 6.

11. The method of claim 10, wherein one or more of R$^a$, R$^b$, R$^c$, R$^d$, R$^e$ and R$^f$ is selected from at least one of:

a C$_{1-5}$ alkyl group substituted with —CO$_2$R$^x$, —OC(O)R$^x$, —CS$_2$R$^x$, —SC(S)R$^x$, —S(O)OR$^x$, —OS(O)R$^x$, —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, wherein R$^x$, R$^y$ and R$^z$ are independently selected from hydrogen or C$_{1-6}$ alkyl;

a C$_{1-3}$ alkyl group substituted with —CO$_2$R$^x$, —C(O)NR$^y$R$^z$, wherein R$^x$, R$^y$ and R$^z$ are each independently selected from C$_{3-6}$ alkyl;

a group selected from:

wherein R$^y$=R$^z$, and wherein R$^x$, R$^y$ and R$^z$ are each selected from C$_{3-6}$ alkyl; or a group selected from:

wherein R$^y$=R$^z$, and wherein R$^y$ and R$^z$ are selected from C$_{3-6}$ alkyl.

12. The method of claim 10, wherein one of R$^a$, R$^b$, R$^c$, R$^d$, R$^e$ and R$^f$ is a substituted C$_{1-5}$ alkyl group, and the remainder of R$^a$, R$^b$, R$^c$, R$^d$, R$^e$ and R$^f$ are independently selected from H and unsubstituted C$_{1-5}$ alkyl groups.

13. The method of claim 1, wherein [Y$^+$] represents a cyclic cation selected from:

optionally wherein R$^f$ is a substituted C$_{1-5}$ alkyl group, and the remainder of R$^a$, R$^b$, R$^c$, R$^d$, R$^e$ and R$^f$ are independently selected from H and unsubstituted C$_{1-5}$ alkyl groups.

14. The method of claim 1, wherein L$_1$ represents a linking group selected from C$_{1-10}$ alkanediyl groups, C$_{1-10}$ alkenediyl groups, C$_{1-5}$ alkanediyl groups, C$_{2-5}$ alkenediyl groups, —CH$_2$—, —C$_2$H$_4$— or —C$_3$H$_6$—.

15. The method of claim 1, wherein each L$_2$ represents a linking group independently selected from C$_{1-2}$ alkanediyl groups, C$_2$ alkenediyl groups, —CH$_2$— or —C$_2$H$_4$—.

16. The method of claim 1, wherein each EDG represents an electron donating group independently selected from —CO$_2$R$^x$, —OC(O)R$^x$, —CS$_2$R$^x$, —SC(S)R$^x$, —S(O)OR$^x$, —OS(O)R$^x$, —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, wherein R$^x$, R$^y$ and R$^z$ are independently selected from H, C$_{1-6}$ alkyl or C$_{3-6}$ alkyl.

17. The method of claim 16, wherein each -L$_2$-EDG represents an electron donating group independently selected from:

wherein R$^y$=R$^z$, and wherein R$^x$, R$^y$ and R$^z$ are each selected from C$_{3-6}$ alkyl.

18. The method of claim 1, wherein [X$^-$] represents one or more anionic species selected from: hydroxides, halides, perhalides, sulphates, sulphites, sulfonates, sulfonimides, phosphates, phosphites, phosphonates, methides, carboxylates, azolates, carbonates, carbamates, thiophosphates, thiocarboxylates, thiocarbamates, thiocarbonates, xanthates, thiosulfonates, thiosulfates, nitrate, nitrite, tetrafluoroborate, hexafluorophosphate, halometallates, amino acids, borates, polyfluoroalkoxyaluminates; or one or more anionic species selected from:
 a) a halide anion selected from: F$^-$, Cl$^-$, Br$^-$, I$^-$;
 b) a perhalide anion selected from: [I$_3$]$^-$, [I$_2$Br]$^-$, [IBr$_2$]$^-$, [Br$_3$]$^-$, [Br$_2$Cl]$^-$, [BrCl$_2$]$^-$, [ICl$_2$]$^-$, [I$_2$Cl]$^-$, [Cl$_3$]$^-$;
 c) an anion selected from: [N$_3$]$^-$, [NCS]$^-$, [NCSe]$^-$, [NCO]$^-$, [CN]$^-$;
 d) a sulphate anion selected from: [HSO$_4$]$^-$, [SO$_4$]$^{2-}$, [R$^2$OSO$_2$O];

e) a sulphite anion selected from: $[HSO_3]^-$, $[SO_3]^{2-}$, $[R^2OSO_2]^-$;
f) a sulfonate anion selected from: $[R^1SO_2O]^-$;
g) a sulfonimide anion selected from: $[(R^1SO_2)_2N]^-$;
h) a phosphate anion selected from: $[H_2PO_4]^-$, $[HPO_4]^{2-}$, $[PO_4]^{3-}$, $[R^2OPO_3]^{2-}$, $[(R^2O)_2PO_2]^-$;
i) a phosphite anion selected from: $[H_2PO_3]^-$, $[HPO_3]^{2-}$, $[R^2OPO_2]^{2-}$, $[(R^2O)_2PO]^-$;
j) a phosphonate anion selected from: $[R^1PO_3]^{2-}$, $[R^1P(O)(OR^2)O]^-$;
k) a methide anion selected from: $[(R^1SO_2)_3C]^-$;
l) a borate anion selected from: [bisoxalatoborate], [bismalonatoborate] tetrakis[3,5-bis(trifluoromethyl)phenyl]borate, tetrakis(pentafluorophenyl)borate;
m) a carboxylate anion selected from: $[R^2CO_2]^-$;
n) an azolate anion selected from: [3,5-dinitro-1,2,4-triazolate], [4-nitro-1,2,3-triazolate], [2,4-dinitroimidazolate], [4,5-dinitroimidazolate], [4,5-dicyanoimidazolate], [4-nitroimidazolate], [tetrazolate];
o) a sulfur-containing anion selected from: thiocarbonates, thiocarbamates, thiocarboxylates, thiophosphates, thiosulfonates, thiosulfates;
p) a nitrate or nitrite anion;
q) a tetrafluoroborate, hexafluorophosphate, hexafluoroantimonate or perchlorate anion;
r) a carbonate anion selected from $[CO_3]^{2-}$, $[HCO_3]^-$, $[R^2CO_3]^-$;
s) polyfluoroalkoxyaluminate anions selected from $[Al(OR^F)_4^-]$, wherein $R^F$ is selected from $C_{1-6}$ alkyl substituted by one or more fluoro groups;
where: $R^1$ and $R^2$ are independently selected from the group consisting of $C_1$-$C_{10}$ alkyl, $C_6$ aryl, $C_1$-$C_{10}$ alkyl($C_6$)aryl and $C_6$ aryl($C_1$-$C_{10}$)alkyl each of which may be substituted by one or more groups selected from: fluoro, chloro, bromo, iodo, $C_1$-$C_6$ alkoxy, $C_2$-$C_{12}$ alkoxyalkoxy, $C_3$-$C_8$ cycloalkyl, $C_6$-$C_{10}$ aryl, $C_7$-$C_{10}$ alkaryl, $C_7$-$C_{10}$ aralkyl, —CN, —OH, —SH, —NO$_2$, —CO$_2R^x$, —OC(O)$R^x$, —C(O)$R^x$, —C(S)$R^x$, —CS$_2R^x$, —SC(S)$R^x$, —S(O)($C_1$-$C_6$ alkyl, —S(O)O($C_1$-$C_6$)alkyl, —OS(O)($C_1$-$C_6$)alkyl, —S($C_1$-$C_6$)alkyl, —S—S($C_1$-$C_6$) alkyl, —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)N R$^y$R$^z$, —C(S)NR$^y$R$^z$, —NR$^y$R$^z$, or a heterocyclic group, wherein $R^x$, $R^y$ and $R^z$ are independently selected from hydrogen or $C_1$-$C_6$ alkyl, or wherein $R^1$ is fluorine, chlorine, bromine or iodine; or
one or more anionic species selected from bistriflimide, triflate, tosylate, perchlorate, $[Al(OC(CF_3)_3)_4^-]$, tetrakis[3,5-bis(trifluoromethyl)phenyl]borate, tetrakis(pentafluorophenyl)borate, tetrafluoroborate, hexfluoroantimonate and hexafluorophosphate anions.

19. The method of claim 1, wherein [Cat$^+$] represents one or more ionic species having the structure:

where: [Z$^+$] is selected from ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium, or uronium.

20. The method of claim 1, wherein the composition further comprises a lower viscosity ionic liquid, optionally wherein the cation of the lower viscosity ionic liquid is selected from:
ammonium, benzimidazolium, benzofuranium, benzothiophenium, benzotriazolium, borolium, cinnolinium, diazabicyclodecenium, diazabicyclononenium, 1,4-diazabicyclo[2.2.2]octanium, diazabicyclo-undecenium, dithiazolium, furanium, guanidinium, imidazolium, indazolium, indolinium, indolium, morpholinium, oxaborolium, oxaphospholium, oxazinium, oxazolium, iso-oxazolium, oxothiazolium, phospholium, phosphonium, phthalazinium, piperazinium, piperidinium, pyranium, pyrazinium, pyrazolium, pyridazinium, pyridinium, pyrimidinium, pyrrolidinium, pyrrolium, quinazolinium, quinolinium, iso-quinolinium, quinoxalinium, quinuclidinium, selenazolium, sulfonium, tetrazolium, thiadiazolium, iso-thiadiazolium, thiazinium, thiazolium, iso-thiazolium, thiophenium, thiuronium, triazinium, triazolium, iso-triazolium and uronium groups; or
$[N(R^3)(R^4)(R^5)(R^6)]^+$ and $[P(R^3)(R^4)(R^5)(R^6)]^+$ wherein $R^3$, $R^4$, $R^5$ and $R^6$ are each independently selected from optionally substituted $C_{1-20}$ alkyl, $C_{3-8}$ cycloalkyl and $C_{6-10}$ aryl groups;
$[P(R^3)(R^4)(R^5)(R^6)]^+$, wherein $R^3$, $R^4$, $R^5$ are selected from $C_{1-10}$ alkyl or $C_{2-6}$ alkyl, and $R^6$ is selected from $C_{4-20}$ alkyl or $C_{8-14}$ alkyl;
$[N(R^3)(R^4)(R^5)(R^6)]^+$, wherein $R^3$, $R^4$, $R^5$ are selected from $C_{4-14}$ alkyl or $C_{6-10}$ alkyl, and $R^6$ is selected from $C_{1-4}$ alkyl or $C_{1-2}$ alkyl; or
imidazolium cations substituted with one or more $C_{1-20}$ alkyl, $C_{3-8}$ cycloalkyl and $C_{6-10}$ aryl groups, or substituted with two $C_{1-10}$ alkyl groups.

21. The method of claim 20, wherein the anion of the lower viscosity ionic liquid comprises one or more anionic species selected from: hydroxides, halides, perhalides, sulphates, sulphites, sulfonates, sulfonimides, phosphates, phosphites, phosphonates, methides, carboxylates, azolates, carbonates, carbamates, thiophosphates, thiocarboxylates, thiocarbamates, thiocarbonates, xanthates, thiosulfonates, thiosulfates, nitrate, nitrite, tetrafluoroborate, hexafluorophosphate, perchlorate, halometallates, amino acids, borates, polyfluoroalkoxyaluminates; or
one or more anionic species selected from:
a) a halide anion selected from: F$^-$, Cl$^-$, Br$^-$, I$^-$;
b) a perhalide anion selected from: $[I_3]^-$, $[I_2Br]^-$, $[IBr_2]^-$, $[Br_3]^-$, $[Br_2Cl]^-$, $[BrCl_2]^-$, $[ICl_2]^-$, $[I_2Cl]^-$, $[Cl_3]^-$;
c) an anion selected from: $[N_3]^-$, $[NCS]^-$, $[NCSe]^-$, $[NCO]^-$, $[CN]^-$;

d) a sulphate anion selected from: $[HSO_4]^-$, $[SO_4]^{2-}$, $[R^2OSO_2O]^-$;
e) a sulphite anion selected from: $[HSO_3]^-$, $[SO_3]^{2-}$, $[R^2OSO_2]^-$;
f) a sulfonate anion selected from: $[R^1SO_2O]^-$;
g) a sulfonimide anion selected from: $[(R^1SO_2)_2N]^-$;
h) a phosphate anion selected from: $[H_2PO_4]^-$, $[HPO_4]^{2-}$, $[PO_4]^{3-}$, $[R^2OPO_3]^{2-}$, $[(R^2O)_2PO_2]^-$;
i) a phosphite anion selected from: $[H_2PO_3]^-$, $[HPO_3]^{2-}$, $[R^2OPO_2]^{2-}$, $[(R^2O)_2PO]^-$;
j) a phosphonate anion selected from: $[R^1PO_3]^{2-}$, $[R^1P(O)(OR^2)O]^-$;
k) a methide anion selected from: $[(R^1SO_2)_3C]^-$;
l) a borate anion selected from: [bisoxalatoborate], [bis-malonatoborate] tetrakis[3,5-bis(trifluoromethyl)phenyl]borate, tetrakis(pentafluorophenyl)borate;
m) a carboxylate anion selected from: $[R^2CO_2]^-$;
n) an azolate anion selected from: [3,5-dinitro-1,2,4-triazolate], [4-nitro-1,2,3-triazolate], [2,4-dinitroimidazolate], [4,5-dinitroimidazolate], [4,5-dicyano-imidazolate], [4-nitroimidazolate], [tetrazolate];
o) a sulfur-containing anion selected from: thiocarbonates, thiocarbamates, thiocarboxylates, thiophosphates, thiosulfonates, thiosulfates;
p) a nitrate or nitrite anion;
q) a tetrafluoroborate, hexafluorophosphate, hexfluoroantimonate or perchlorate anion;
r) a carbonate anion selected from $[CO_3]^{2-}$, $[HCO_3]^-$, $[R^2CO_3]^-$; preferably $[MeCO_3]^-$;
s) polyfluoroalkoxyaluminate anions selected from $[Al(OR^F)_4^-]$, wherein $R^F$ is selected from $C_{1-6}$ alkyl substituted by one or more fluoro groups:

where: $R^1$ and $R^2$ are independently selected from the group consisting of $C_1$-$C_{10}$ alkyl, $C_6$ aryl, $C_1$-$C_{10}$ alkyl($C_6$)aryl and $C_6$ aryl($C_1$-$C_{10}$)alkyl each of which may be substituted by one or more groups selected from: fluoro, chloro, bromo, iodo, $C_1$-$C_6$ alkoxy, $C_2$-$C_{12}$ alkoxyalkoxy, $C_3$-$C_8$ cycloalkyl, $C_6$-$C_{10}$ aryl, $C_7$-$C_{10}$ alkaryl, $C_7$-$C_{10}$ aralkyl, —CN, —OH, —SH, —NO$_2$, —CO$_2R^x$, —OC(O)$R^x$, —C(O)$R^x$, —C(S)$R^x$, —CS$_{-2}R^x$, —SC(S)$R^x$, —S(O)($C_1$-$C_6$)alkyl, —S(O)O($C_1$-$C_6$)alkyl, —OS(O)($C_1$-$C_6$)alkyl, —S($C_1$-$C_6$)alkyl, —S—S($C_1$-$C_6$ alkyl), —NR$^x$C(O)NR$^y$R$^z$, —NR$^x$C(O)OR$^y$, —OC(O)NR$^y$R$^z$, —NR$^x$C(S)OR$^y$, —OC(S)NR$^y$R$^z$, —NR$^x$C(S)SR$^y$, —SC(S)NR$^y$R$^z$, —NR$^x$C(S)NR$^y$R$^z$, —C(O)NR$^y$R$^z$, —C(S)NR$^y$R$^z$, —NR$^y$R$^z$, or a heterocyclic group, wherein $R^x$, $R^y$ and $R^z$ are independently selected from hydrogen or $C_1$-$C_6$ alkyl, or wherein $R^1$ is fluorine, chlorine, bromine or iodine; or one or more anionic species selected from bistriflimide, triflate, tosylate, perchlorate, $[Al(OC(CF_3)_3)_4^-]$, tetrakis[3,5-bis(trifluoromethyl)phenyl]borate, tetrakis(pentafluorophenyl)borate, tetrafluoroborate, hexfluoroantimonate and hexafluorophosphate anions.

22. The method of claim 20, wherein the ionic liquid is present in the composition in a concentration of at least 0.001 M, or from 0.005 M to 0.01 M.

23. The method of claim 1, wherein the acidic solution is obtainable by leaching the rare earth metal from its source with an acid.

* * * * *

UNITED STATES PATENT AND TRADEMARK OFFICE
CERTIFICATE OF CORRECTION

PATENT NO. : 11,396,684 B2
APPLICATION NO. : 16/469748
DATED : July 26, 2022
INVENTOR(S) : Nockemann et al.

It is certified that error appears in the above-identified patent and that said Letters Patent is hereby corrected as shown below:

On the Title Page

Column 1, Item (30):
"Foreign Application Priority Data: Dec. 16, 2016 (GB)... 1621523"

Should Read:
--Foreign Application Priority Data: Dec. 16, 2016 (GB)... 1621523.8--

Signed and Sealed this
Thirty-first Day of January, 2023

Katherine Kelly Vidal
*Director of the United States Patent and Trademark Office*